US011804690B2

(12) United States Patent
Do et al.

(10) Patent No.: US 11,804,690 B2
(45) Date of Patent: Oct. 31, 2023

(54) LASER ASSEMBLY FOR AN OPTOACOUSTIC PROBE

(71) Applicant: Seno Medical Instruments, Inc., San Antonio, TX (US)

(72) Inventors: Tam Do, San Antonio, TX (US); Xavier Saenz, San Antonio, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 423 days.

(21) Appl. No.: 17/095,587

(22) Filed: Nov. 11, 2020

(65) Prior Publication Data

US 2022/0149585 A1     May 12, 2022

(51) Int. Cl.
| | |
|---|---|
| *H01S 3/115* | (2006.01) |
| *H01S 3/06* | (2006.01) |
| *A61B 5/00* | (2006.01) |
| *H01S 3/102* | (2006.01) |
| *H01S 3/107* | (2006.01) |
| *H01S 3/067* | (2006.01) |
| *H01S 3/13* | (2006.01) |
| *H01S 3/10* | (2006.01) |

(52) U.S. Cl.
CPC ............ *H01S 3/115* (2013.01); *A61B 5/0095* (2013.01); *H01S 3/0627* (2013.01); *H01S 3/107* (2013.01); *H01S 3/1024* (2013.01); *H01S 3/06708* (2013.01); *H01S 3/10038* (2013.01); *H01S 3/1305* (2013.01)

(58) Field of Classification Search
CPC ..................... H01S 3/1123–127; A61B 5/0095
See application file for complete search history.

(56) References Cited

U.S. PATENT DOCUMENTS

| | | | | |
|---|---|---|---|---|
| 5,226,051 A | * | 7/1993 | Chan ....................... | H01S 3/115 372/38.03 |
| 6,078,606 A | * | 6/2000 | Naiman .................. | F41G 3/145 372/17 |
| 6,418,154 B1 | * | 7/2002 | Kneip ..................... | H01S 3/1312 372/75 |
| 7,929,579 B2 | * | 4/2011 | Hohm ................... | A61B 18/203 372/18 |
| 9,528,936 B2 | * | 12/2016 | Schmid .............. | G01N 21/1702 |

(Continued)

FOREIGN PATENT DOCUMENTS

| | | | | |
|---|---|---|---|---|
| JP | 4169187 B2 | * | 10/2008 | ......... H01S 3/10092 |
| JP | 4877692 B2 | * | 2/2012 | ......... H01S 3/10092 |

(Continued)

*Primary Examiner* — Joshua King
(74) *Attorney, Agent, or Firm* — THE SMALL PATENT LAW GROUP LLC; Josef L. Hoffmann

(57) ABSTRACT

A laser assembly is provided that includes a laser resonator that emits a first light having a first pulse width, and a trigger assembly electrically coupled to the laser resonator to actuate the laser resonator. The laser assembly also includes a sensor configured to detect the first light as the light emits from the laser resonator, and one or more processors coupled to the trigger assembly. The one or more processors are configured to obtain a first time delay interval from when the trigger assembly is actuated to when the sensor detects the first light, and actuate the laser resonator to emit a second light having a second pulse width based on the time delay interval determined.

13 Claims, 6 Drawing Sheets

(56) References Cited

U.S. PATENT DOCUMENTS

| | | | | |
|---|---|---|---|---|
| 9,825,421 | B2 * | 11/2017 | Jhon | H01S 3/1109 |
| 2011/0267671 | A1 * | 11/2011 | Peng | H01S 3/115 |
| | | | | 359/341.1 |
| 2011/0319743 | A1 * | 12/2011 | Satoh | A61B 5/0035 |
| | | | | 600/407 |
| 2013/0116538 | A1 * | 5/2013 | Herzog | A61B 8/4281 |
| | | | | 600/407 |
| 2013/0276542 | A1 * | 10/2013 | Herzog | G01J 1/04 |
| | | | | 73/655 |
| 2013/0281819 | A1 * | 10/2013 | Schmid | A61B 5/14542 |
| | | | | 600/407 |
| 2015/0075287 | A1 * | 3/2015 | Herzog | G01H 9/008 |
| | | | | 73/655 |
| 2016/0317038 | A1 * | 11/2016 | Zalev | A61B 8/0825 |
| 2016/0352068 | A1 * | 12/2016 | Jhon | H01S 3/115 |
| 2017/0324212 | A1 * | 11/2017 | Jhon | H01S 3/1305 |
| 2019/0150749 | A1 * | 5/2019 | Harris | A61B 5/0095 |
| 2022/0071493 | A1 * | 3/2022 | Feldman | H01S 3/10061 |

FOREIGN PATENT DOCUMENTS

| | | | | |
|---|---|---|---|---|
| WO | WO-2008086989 A1 * | 7/2008 | | G01S 7/484 |
| WO | WO-2013046569 A1 * | 4/2013 | | A61B 5/0095 |
| WO | WO-2013076986 A1 * | 5/2013 | | A61B 5/0095 |
| WO | WO-2017146331 A1 * | 8/2017 | | B23K 26/00 |
| WO | WO-2018087895 A1 * | 5/2018 | | G03F 7/70033 |

\* cited by examiner

LASER ASSEMBLY FOR AN OPTOACOUSTIC PROBE

TECHNICAL FIELD

The present invention relates in general to the field of medical imaging, and in particular to a system relating to an optoacoustic probe.

BACKGROUND

Optoacoustic imaging systems visualize thin tissue slices at a tissue site. A tissue site may contain a variety of tissue structures that may include, for example, tumors, blood vessels, tissue layers, and components of blood. In optoacoustic imaging systems, light is used to deliver optical energy to a planer slice of the tissue site, which as a result of optical absorption with the tissue structures, produce acoustic waves. An image spatially representing the tissue site can be generated by performing image reconstruction on acoustic signals that return to an ultrasound transducer array. Because biological tissue scatters impinging optical energy in many directions the optical energy can be absorbed by tissue structures outside of a targeted region, which can generate acoustic return signals that interferes with the imaging of tissue structures within the targeted region.

A laser assembly typically provides the optical energy required to generate the acoustic waves. The laser assembly often provides two separate lasers, with two laser pumps generating light at different wavelengths. The laser assembly may also be embodied by a single laser pump capable of generating light at different wavelength using an optical parametric oscillator (OPO) to generate different wavelengths of light. The laser pumps may also be blanked, impeded, etc. in order to provide a pulsed light output.

The properties of the excitation of the laser are important parameters that affect the photoacoustic image quality. The laser pulse width is closely related to both signal strength and image resolution. In addition, the photoacoustic temporal waveform shows sharper, and is improved, as the pulse width is shorter, which also indicates high frequency signal components have increased. The width of the first peak on the temporal waveform is corresponding to the pulse width. The modulation transfer function shows that image resolution improves as the pulse width is narrowed.

BRIEF SUMMARY

New and useful systems, apparatuses, and methods for providing optoacoustic imaging are set forth in the appended claims. Illustrative embodiments are also provided to enable a person skilled in the art to make use the claimed subject matter.

Objectives, advantages, and a preferred mode of making and using the claimed subject matter may be understood best by reference to the accompanying drawings in conjunction with the following detailed description of illustrative embodiments.

In accordance with embodiments herein, a laser assembly is provided that includes a laser resonator that emits a first light having a first pulse width, and a trigger assembly electrically coupled to the laser resonator to actuate the laser resonator. The laser assembly also includes a sensor configured to detect the first light as the light emits from the laser resonator, and one or more processors coupled to the trigger assembly. The one or more processors are configured to obtain a first time delay interval from when the trigger assembly is actuated to when the sensor detects the first light, and actuate the laser resonator to emit a second light having a second pulse width based on the time delay interval determined.

Optionally, the one or more processors are also configured to obtain a first full width half max pulse width of the first light, and actuate the laser resonator to emit the second light having the second pulse width based on the first full width half max pulse width. In one aspect, the one or more processors actuate the laser resonator to emit the second light based on a proportion between the time delay and the first full width half max pulse width. In another aspect, the one or more processors are further configured to determine a first pulse-width controller input based on the first full width half max pulse width, and actuate the laser resonator to emit the second light based on the first pulse-width controller input.

Optionally, the one or more processors are further configured to obtain a first energy output of the first light based of the first light detected by the sensor, and actuate the laser resonator to emit the second light having the second pulse width based on the energy output determined. In one aspect, the one or more processors are further configured to determine a first energy controller input based on the first energy output obtained, and obtain a second energy output of the second light based on the first energy controller input. In one example, the trigger assembly is electrically coupled to an energy controller configured to receive the first energy output and determine a first energy controller input. Alternatively, the trigger assembly is electrically coupled to a pulse-width controller configured to receive a first full width half max pulse width and determine a first pulse-width controller input. In one embodiment, the sensor includes a photodiode. In another embodiment, the trigger assembly is a Q-switch trigger assembly.

In one or more embodiment, a computer implemented method is provided that includes receiving from a trigger assembly a first signal generated from actuating a trigger device to provide a first light from a laser assembly, and receiving from a sensor a second signal generated from the first light having a first pulse width emitting in response to the first signal. The method also includes obtaining a first time delay interval from when the trigger device is actuated to when the sensor detects the first light, and actuating the laser assembly to emit a second light having a second pulse width based on the time delay interval obtained.

Optionally, the method also includes obtaining a first full width half max pulse width of the first light, and actuating the laser assembly to emit the second light having the second pulse width based on the first full width half max pulse width. In one aspect, actuating the laser assembly to emit the second light is based on a proportion between the time delay and the first full width half max pulse width. In another aspect, the method also includes determining a first pulse-width controller input based on the first full width half max pulse width, and actuating the laser assembly to emit the second light based on the first pulse-width controller input.

Optionally, the method also includes obtaining a first energy output of the first light based of the first light detected by the sensor, and actuating the laser assembly to emit the second light having the second pulse width based on the energy output determined. In one aspect, the method also includes determining a first energy controller input based on the first energy output obtained, and obtaining a second energy output of the second light based on the first energy controller input. In one example, the sensor is a photodiode.

In one or more embodiments, a laser assembly is provided that includes a laser resonator that emits a first light having a first pulse width, and a trigger assembly electrically coupled to the laser pump camber to actuate the laser resonator. The laser assembly also includes a photodiode configured to detect the first light as the light emits from the laser resonator, and an energy controller electrically coupled to the photodiode and configured to determine a first energy controller input based on an energy output of the first light. The laser assembly also includes a pulse-width controller electrically coupled to the photodiode and configured to determine a first pulse-width controller input based on a first full width half max pulse width of the first light, and one or more processors coupled to the trigger assembly and photodiode. The one or more processors are configured to actuate the laser resonator to emit a second light having a second pulse width based on the first energy controller input and first pulse-width controller input.

Optionally, the pulse-width controller is also configured to determine a time delay between when the trigger assembly communicates an actuation signal to the laser resonator, and when the photodiode detects the first light, and determine the first pulse-width controller input based on the time delay and the first full width half max pulse width. In one aspect, the first pulse-width controller input is based on a proportion between the time delay and the first full width half max pulse width.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

Figure 1:
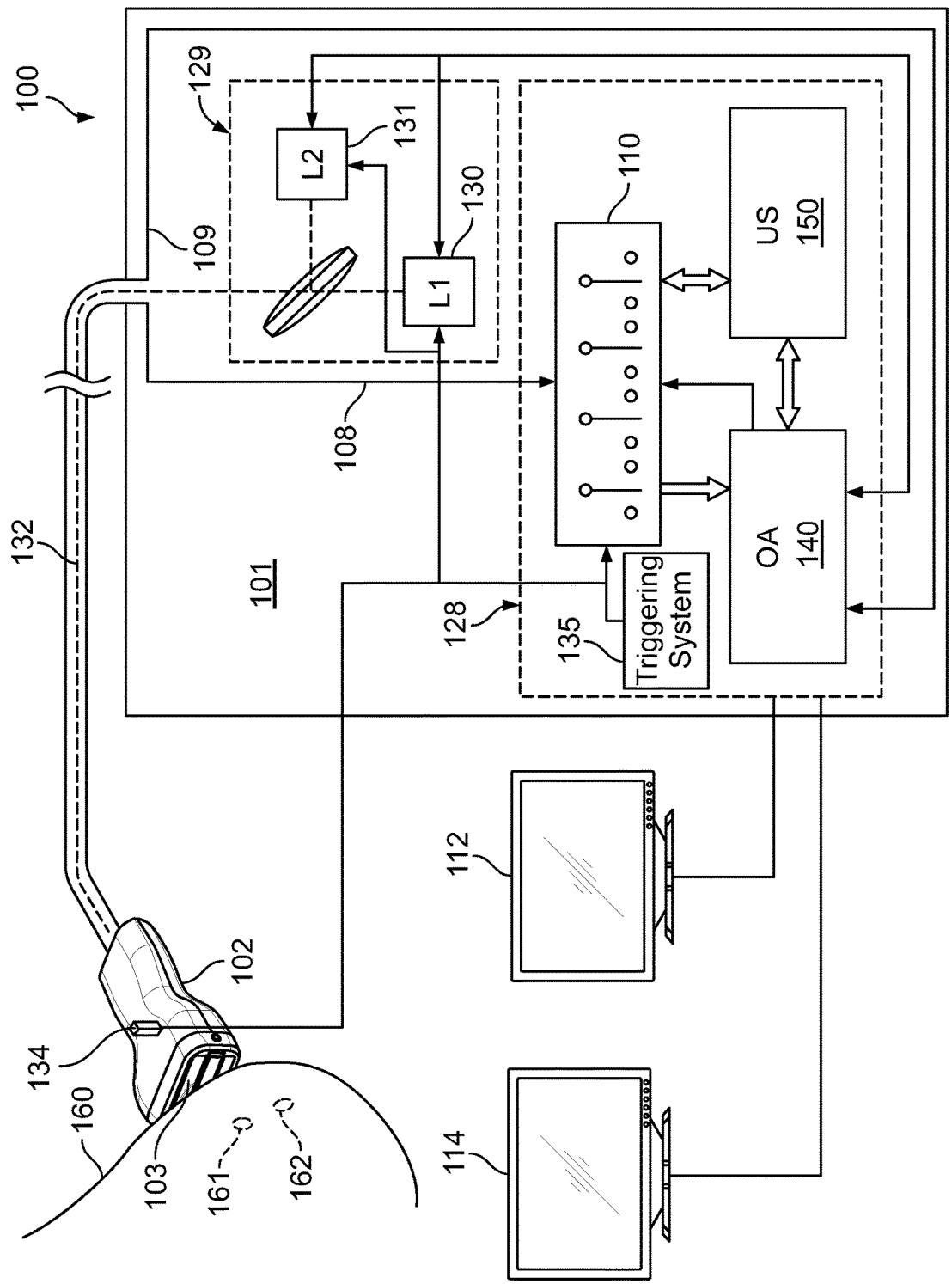
FIG. 1 shows a schematic block diagram illustrating an embodiment of a combined optoacoustic and ultrasound system that may be used as a platform for the methods and devices disclosed herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations, and algorithms, can be implemented by means of analog or digital hardware and computer program instructions.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases, frequency domain-based algorithms require zero or symmetric padding for performance. This padding is not essential to describe the embodiment of the algorithm, so it is sometimes omitted from the description of the processing steps. In some cases, where padded is disclosed in the steps, the algorithm may still be carried out without the padding. In some cases, padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Embodiments herein may be implemented in connection with one or more of the systems and methods described in one or more of the following patents, publications, and/or published applications, all of which are expressly incorporated herein by reference in their entireties:

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015

U.S. Publication 2016/0187481, titled "Opto-Acoustic Imaging System With Detection Of Relative Orientation Of Light Source And Acoustic Receiver Using Acoustic Waves" filed Oct. 30, 2015.

As used herein the term "light" shall refer to any and all electromagnetic radiation, including but not limited to UV radiation, visible light, infrared radiation, etc. Light as used herein is in no way limited to the visible spectrum. Light may include characteristics including polarization, wavelength, frequency, etc. When a characteristic of light is changed, enhanced, diminished, altered, etc. the light may be considered converted, changed, enhanced, diminished, altered, etc.

A laser assembly is provided that utilizes a single sensor at the output of a laser resonator to determine the time delay from the time a trigger assembly is actuated to the time light is emitted from the laser resonator. In one example the sensor is a photodiode that converts the detected light into current such that determinations can be made regarding the energy and pulse-width of the light. In addition, the sensor monitors the output energy of the laser resonator independent of signal amplitude. The time delay and energy output are then utilized as feedback to control the width and energy of the laser pulse.

Turning to FIG. 1, generally, device 100 provides an optoacoustic system that may also be employed as multi-modality, combined optoacoustic and ultrasound system. In an embodiment, the device 100 includes a probe 102 connected via a light path 132 and an electrical path 108 to a system chassis 101. Within the system chassis 101 is housed a laser assembly 129 and a computing subsystem 128.

The computing subsystem 128 includes one or more computing components for ultrasound control and analysis and optoacoustic control and analysis; these components may be separate, or integrated. In an embodiment, the computing subsystem comprises a relay system 110, a triggering system 135, an optoacoustic processing and overlay system 140 and an ultrasound instrument 150. In one embodiment, the triggering system 135 is configured to actuate and control operation of laser pump chamber 130.

The laser pump chamber 130 is utilized in creating signals for imaging purposes as will be described in greater detail with reference to FIGS. 3-4. In an embodiment, the laser assembly 129 is capable of producing pulses of light of at least two different wavelengths. The output of the laser pump chamber 130 of the laser assembly 129 is delivered to the probe 102 via the light path 132. The laser light is emitted on a targeted area, such as a breast or prostrate, resulting in soundwaves being formed as a result of the laser bouncing of objects. These soundwaves are then utilized by the ultrasound control to provide imaging of the targeted area for analysis.

One or more displays 112, 114, which may be touch screen displays, are provided for displaying images and all or portions of the device 100 user interface. One or more other user input devices (not shown) such as a keyboard, mouse, and various other input devices (e.g., dials and switches) may be provided for receiving input from an operator.

Figure 2:
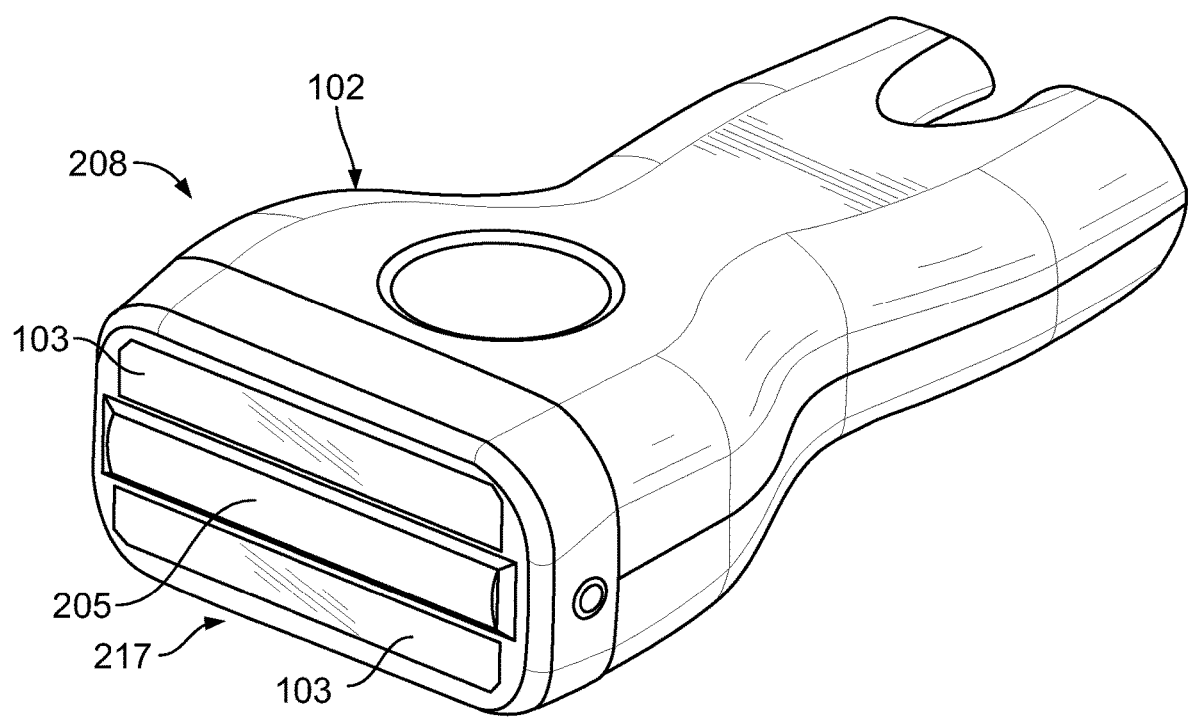
FIG. 2 shows a schematic orthogonal view of an embodiment of a probe that may be used in connection with the methods and other devices disclosed herein.

Turning now to FIG. 2, the probe 102 includes an ultrasound transducer covered by an acoustic lens 205. The probe 102 includes distal and proximal ends. A probe face 217 of the probe 102 is at the distal end 208. The probe 102 also includes one or more optical windows 103 through which the light is carried on light path 132 can be transmitted to the surface of a volume 160, for example, a three-dimensional volume. Specifically, the probe 102 may be placed in close proximity with organic tissue, phantom or other volume 160 that may have one or more inhomogeneities 161, 162, such as e.g., a tumor, within. An ultrasound gel (not shown) or other material may be used to improve acoustic coupling between the probe 102 and the surface of the volume 160 and/or to improve optical energy transfer.

Figure 3:
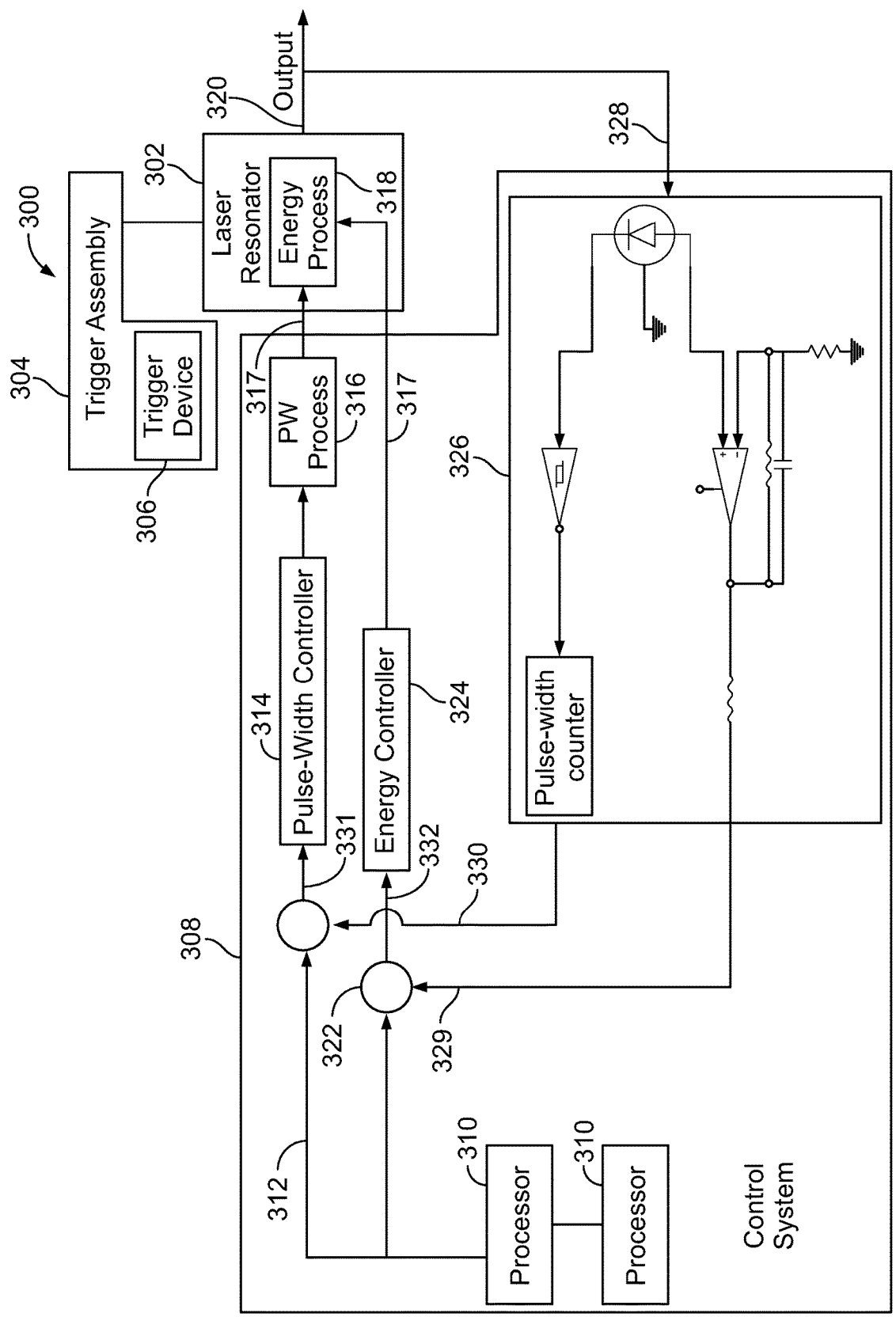
FIG. 3 shows a schematic view of a laser assembly used in connection with the methods and other devices disclosed herein.

Turning now to FIG. 3. FIG. 3 is a schematic view of an example embodiment of a laser assembly 300. In one embodiment, the laser assembly 300 of FIG. 3 is the laser assembly 129 of FIG. 1. The laser assembly 300 includes a laser resonator 302. The laser resonator 302 may include light generating materials, including Nd:YAG, Alexandrite, or the like. The laser resonator 302 may include a single cavity or multiple cavities. The laser resonator 302 can emit light including to UV radiation, visible light, infrared radiation, etc.

The laser assembly 300 may be provided with optics that modify the light emitted by the laser resonator 302 to produce different wavelengths of light, different polarizations of light, different direction of light, etc. For example, a beam splitter may be implemented to produce a first light and a second light. The second light may then be emitted through lens arrangements to modify the wavelength of the second light to be different than the wavelength of the first light.

The laser assembly 300 also includes a trigger assembly 304 that includes a trigger device 306 that is operably coupled to the laser resonator 302. The trigger device 306 in one example is a footswitch coupled to the probe. Alternatively the trigger device 306 can be a push button, an input at a computing device, such as a keyboard, or a touchscreen, or the like. The trigger assembly 304 includes the trigger device 306, along with supporting structure, and can also include a control system and circuitry associated with the trigger device 306. The trigger assembly 304 signals the laser resonator 302 to provide the light output 320. In one example, the trigger assembly 304 is a Q-switch trigger assembly.

The laser assembly 300 also includes a control system 308 that includes one or more processors 310. The control system 308 includes a pulse-width set point 312 that provides a pulse-width controller input 331 for a pulse-width controller 314. The pulse-width controller 314 operates a pulse-width process 316 that provides an energy process input 317 for an energy process 318 for emitting a light output 320 with a controlled pulse-width. Specifically, the energy process input 317 provides a value that approximates the fixed pulse-width set point 312. Pulse-width input 330 from the light output 320 is then utilized as feedback for the control system 308 where the pulse-width input 330 and pulse-width set point 312 are both used to determine the light output 320.

The control system 308 also includes the energy set point 322 that provides an energy controller input 332 for an energy controller 324 that also provides an input for the energy process 318 to provide the light output 320 with a controlled energy. The energy input 329 from the light output 320 is then utilized as feedback for the control system 308 similar to how the pulse-width input 330 is utilized as feedback for the control system 308. In this instance, both the energy input 329 and energy set point 322 are utilized to determine the light output 320 as well. For each iteration of light emitted, energy input and pulse-width input are used to determine the energy process input 317 for an energy process 318. In one example, a plurality of sequential energy outputs are produced, the first energy output, then a second energy output, then a third energy output, etc. and the energy output from each light output is utilized to determine the subsequent energy controller input 322 (i.e., second energy set point, third energy set point, etc.), and the subsequent pulse-width input is utilized to determine the subsequent pulse-width controller input 312, (i.e., second pulse-width set point, third pulse-width set point, etc.).

The laser assembly 300 also includes a sensor 326 that in one example is a photodiode. The sensor is coupled to the laser resonator 302 to detect when the light is output by the laser resonator 302. Specifically, the light output in one example is a first light having a first pulse width. From the light output 320 of the first light, the sensor 326 provides the energy output 328 to update the energy controller input 332. Similarly, the sensor 326 also has a pulse-width counter to provide a pulse-width input 330 to update the pulse-width controller input 331.

In an embodiment when the sensor 326 is a photodiode, the photodiode converts the light into current. That current may then be utilized by circuitry to determine the energy output of the light in order to modify the energy controller input 332. Additionally, the current may also be utilized in association with the pulse-width counter to determine and modify the pulse-width controller input 331. In this manner, the pulse-width controller input 331 also receives an input from the trigger assembly 304. In addition, by utilizing the input (from trigger assembly 304), the time delay from when the trigger device 306 is actuated, and when the light that is emitted by the laser resonator 302 can be determined. Based on the updated pulse-width counter 326 and energy set point, the laser resonator is actuated to emit a second light having a second pulse width with a pulse-width counter measurement nearing the pulse-width setpoint and/or energy input nearing the energy set point as a result of the pulse-width controller input 331 and energy controller input 332. In one example, only one of the pulse width set point 312 or energy set point 322 is approximated using the pulse-width controller input 331, or energy controller input 332 to provide the light output 320. Alternatively, both the pulse width set point 312, and energy set point 322 are combined and approximated simultaneously to provide the light output 320.

In an example, a first light may have a pulse every 10 ms with an output energy of 10 Joules/(sec*m^2) where the energy is determined from the full width half max pulse width (FWHM) of the pulse. From the time of the trigger to the photodiode detecting light may be 5 ms. In or example, the circuitry coupled to the photodiode is configured to determine the time delay based on the amount of time between the trigger event and the detection of an energy peak. Then knowing the delay, the 10 ms pulse is determined. In order to adjust the laser assembly, the pulse may be shortened during a next interval to every 6 ms, while the laser assembly adjusts the power output to ensure the FWHM of 10 Joules/(sec*m^2) are still being provided.

In this manner, the light detected from the photodiode may be utilized as feedback to adjust the energy controller input and the pulse-width controller input. As a result, the FWHM of the laser pulse is maintained by adjusting the energy in the laser resonator by voltage control of the excitation source. Once the desired pulse width is achieved (based on the pulse-width set point 312) the output radiant energy is adjusted using feedback from the sensor. This radiant energy is controlled by an attenuator at the output of the laser resonator.

Figure 4:
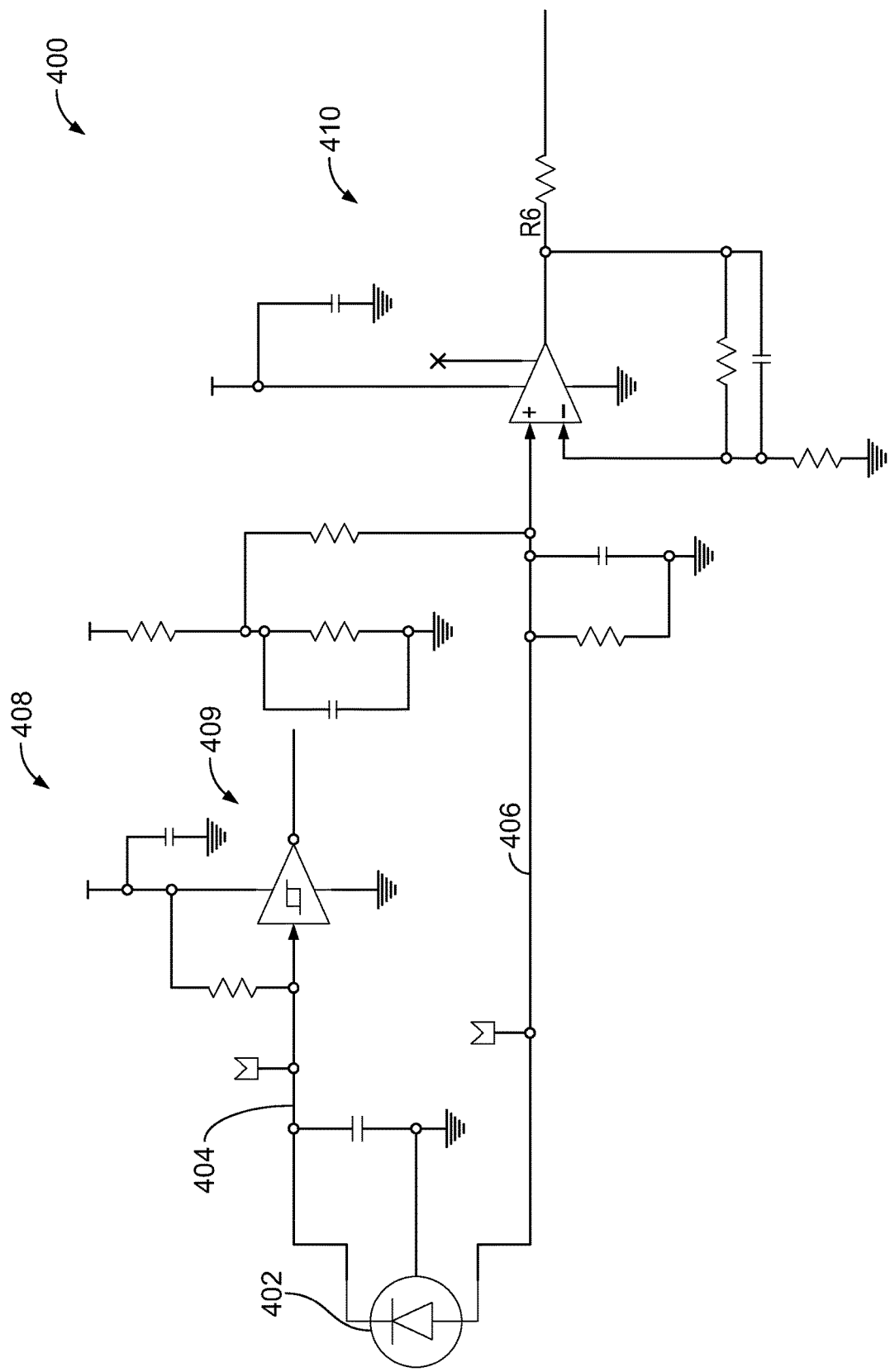
FIG. 4 is a schematic diagram of a sensor used in connection with the methods and other devices disclosed herein.

Turning now to FIG. 4. FIG. 4 illustrates an example sensor 400 that in one example is the sensor 326 of FIG. 3. The sensor 400 includes a sensing element 402 that in one example is a photodiode. The sensing element 402 is coupled between a cathode 404 and an anode 406. The cathode 404 is coupled to a pulse width counter 408. The pulse width counter determines the pulse width of a first light, second light, etc. and also is used to provided timing data that is used to determine the time delay between a trigger device being actuated and the first light, second light, etc. being detected.

When light is emitted from a laser resonator the light hits the sensor element 402 and creates a current that syncs the trigger output 409 of the circuit at the exact lasing instance. In one example, the trigger output 409 is utilized for co-registration. The trigger timing is then measured relative to a trigger assembly to calculate the time delay. In this manner, the pulse width counter 408 provides an input for a pulse-width set point. The trigger output and/or the time delay are used to temporally adjust the optoacoustic image. In one example, the trigger output can be used to signal the optoacoustic processing and overlay system 140 to begin data acquisition. In another example, the time delay can be used to signal the optoacoustic processing.

Figure 5:
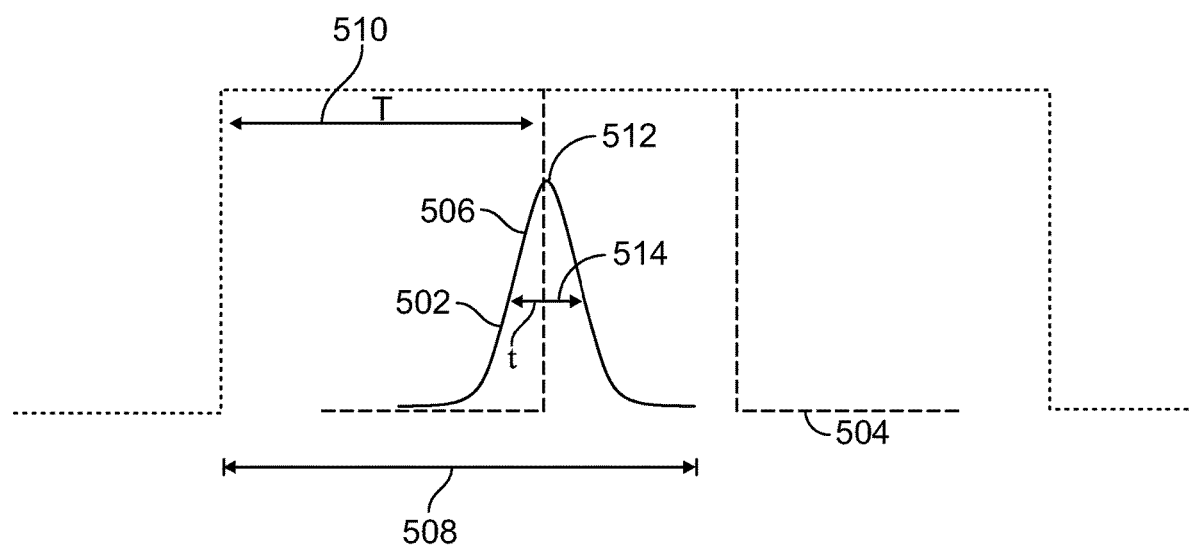
FIG. 5 is a graph of current over time used in connection with the methods and other devices disclosed herein.

With reference to FIG. 5, FIG. 5 illustrates an example of current 502 over time 504 for a first light of a laser pulse used to determine the pulse-width controller input. The pulse 506 is provided by a trigger event, or trigger actuation. The trigger period 508 represents the time of the actuation of a trigger device to the time the pulse 506 is complete. Here, 510 represents a time delay T from the actuation of the trigger device to the peak 512 of the pulse 506, wherein 514 represents a time t that is the full width half max pulse width (FWHM) of the pulse 506. A proportional relationship between the time delay T and the FWHM of the laser pulse is then used to provide feedback to the closed loop system independent of the signal amplitude. In this manner, the pulse-width controller input is determined.

With reference back to FIG. 4, the anode 406 meanwhile is coupled to an energy detector 410. The energy detector 410 determines the amount of energy provided from the first light, second light, etc. The energy output of the first light, second light, etc. may be determined without determining the amplitude of the first light, second light, etc. Instead, the same current produced by the sensor 400 to sync the output trigger is also used to create a voltage proportional to the radiant energy hitting the sensor 400. This provides a pulse to pulse energy measurement of the first energy output, second energy output, etc., for feedback into the closed loop system to maintain the desired radiant fluence while adjusting the FWHM of the laser pulse. In this manner, the energy determination made by the energy detector 410 is utilized to determine the energy controller input.

Figure 6:
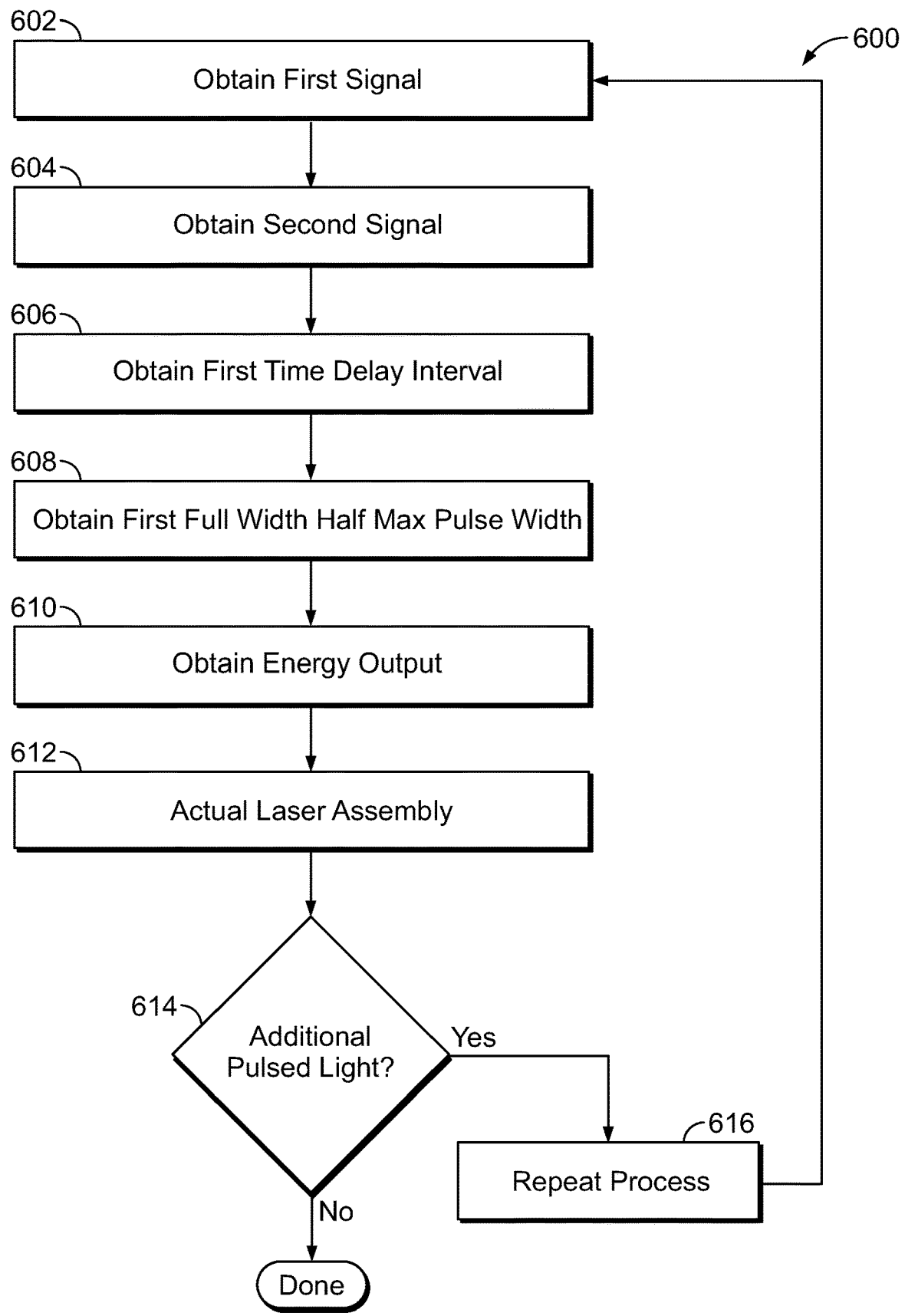
FIG. 6 is a block flow diagram of a process for controlling the pulse-width of light emitted by a laser assembly used in connection with the methods and other devices disclosed herein.

FIG. 6 illustrates a process 600 for controlling the pulse-width of light emitted by a laser assembly. In one example, the laser assembly of FIG. 3 is utilized to perform the process 600. At 602, one or more processors obtain from a trigger assembly a first signal generated from actuating a trigger device to provide a first light from a laser assembly. In one example the trigger device is a push button of a probe. Alternatively, the trigger device is an input on a remote computing device in communication with a probe, and the trigger device can include a touch screen, key input, or the like. Specifically, upon actuation of the trigger device, a signal is communicated to the processor. Such a signal can be communicated through over the air communication, or wirelessly. Alternatively, the signal can be communicated over a wire based channel.

At 604, the one or more processors obtain from a sensor a second signal generated from the first light having a first pulse width emitting in response to the first signal. In particular, the first signal in one embodiment is an actuation signal that causes a laser resonator to emit the first light. The second signal is then generated based on the detection of the first light emitted. In one example, the sensor is a photodiode that detects the light as soon as the light emits from the laser resonator. In particular, the photodiode is positioned adjacent the laser channel of the laser resonator. The photodiode converts the light into electric current that represents the second signal that is obtained by the one or more processors.

At 606, the one or more processors obtain a first time delay interval from when the trigger device is actuated to when the sensor detects a first light. In one embodiment, the sensor detects the peak of the pulse of the first light detected, where the time from actuation of the trigger device to the peak of the first light detected represents the first time delay.

In one example, when the trigger device is actuated, the first signal is communicated to the one or more processors and laser resonator. The first signal results in actuation of the laser resonator, at which time the first light from the laser resonator is emitted. The sensor, that in one embodiment is a photodiode, then detects the light emitted from the laser resonator.

In the embodiment where the sensor is a photodiode, the photodiode converts the detect light into a current. The time delay from the time the trigger device is first actuated to the time of the peak of the current detected by the photodiode is then determined and represents the first time delay interval. Alternatively, the time delay can measure the time from when the trigger device is first actuated to the time current is first detected. In yet another example, the time delay can measure the time from when the trigger device is first actuated to the time current finishes being detected.

At 608, the one or more processors obtain a first full width half max pulse width (FWHM) of the first light. The FWHM is the time required for exactly half the energy of a pulse width to occur. The measurement is taken with the peak of the first light energy used as the midpoint of the FWHM. Based on the first time delay, and specifically a proportional relationship between the first time delay T and the FWHM of the first light (e.g. laser pulse) feedback is provided to the closed loop system independent of the signal amplitude. In particular, the feedback is provided to determine a first pulse-width controller input.

At 610, one or more processors obtain the first energy output of the first light utilizing the sensor. Specifically, the current detected by the sensor is utilized to create a voltage proportional to the radiant energy hitting the sensor. This provides a pulse to pulse energy measurement for feedback into the closed loop system to maintain the desired radiant fluence while adjusting the FWHM of the laser pulse. A first energy controller input is consequently determined based the detected current. The first energy controller input can then be continuously updated as light is emitted by the laser resonator.

At 612, the one or more processors actuate the laser assembly to emit a second light having a second pulse width. Based on the feedback, both the first pulse-width controller input and first energy controller input are utilized to emit a second light having a second pulse width. Once the desired pulse width is achieved the output radiant energy is adjusted using the first pulse-width controller input, and energy controller input feedback from the sensor. This radiant energy is controlled by an attenuator at the output of the laser resonator.

At 614, a determination is made whether additional pulsed light is desired. If not, and the trigger assembly is no longer actuated, the process is done. If at 614, actuation of the trigger device continues, at 616, the process is repeated. So, in one example, the second light with the second pulse-width is analyzed to emit a third light with a third pulse-width. In one example, the second pulse width and the third pulse width are the same. Alternatively, the second pulse width and third pulse with are different.

In all, a laser assembly is provided that can utilize a single sensor at the output of a laser resonator to determine the time delay from the time a trigger assembly is actuated to the time light is emitted from the laser resonator. The sensor monitors the output energy of the laser resonator independent of signal amplitude, while also monitoring the pulse-width count. A control system utilizes these measurements from the sensor in order to modify both an energy controller input and a pulse-width controller input. In this manner, the time delay and energy output are utilized as feedback to control the width and energy of the laser pulse.

By using the laser assembly and process described herein, a cost reduction achieved because only a single sensor, that can have a sensing element that is a photodiode may be utilized to adjust the laser output. Additionally, the quality of image improved as resolution can be maintained. Peak power is also more efficiently maintained, improving patient safety. Also, measurement accuracy is increased as data is collected independent of signal amplitude. Another advantage is that the laser resonator performance maintained as peak power is monitored and damage thresholds not exceeded, reducing wear, and extending laser assembly life.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing example embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces, and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. A laser assembly comprising:
   a laser resonator that emits a first light having a first pulse width;
   a trigger assembly electrically coupled to the laser resonator to actuate the laser resonator;
   a sensor configured to detect the first light as the light emits from the laser resonator;
   one or more processors coupled to the trigger assembly and configured to:
      obtain a first time delay interval from when the trigger assembly is actuated to when the sensor detects the first light; and
      actuate the laser resonator to emit a second light having a second pulse width based on the time delay interval determined.

2. The laser assembly of claim 1, wherein the one or more processors are further configured to:
   obtain a first full width half max pulse width of the first light; and
   actuate the laser resonator to emit the second light having the second pulse width based on the first full width half max pulse width.

3. The laser assembly of claim 2, wherein the one or more processors actuate the laser resonator to emit the second light based on a proportion between the time delay and the first full width half max pulse width.

4. The laser assembly of claim 2, wherein the one or more processors are further configured to:
   determine a first pulse-width controller input based on the first full width half max pulse width; and
   actuate the laser resonator to emit the second light based on the first pulse-width controller input.

5. The laser assembly of claim 1, wherein the one or more processors are further configured to:
   obtain a first energy output of the first light based of the first light detected by the sensor; and
   actuate the laser resonator to emit the second light having the second pulse width based on the energy output determined.

6. The laser assembly of claim 5, wherein the one or more processors are further configured to:
   determine a first energy controller input based on the first energy output obtained; and
   obtain a second energy output of the second light based on the first energy controller input.

7. The laser assembly of claim 5, wherein the trigger assembly is electrically coupled to an energy controller configured to receive the first energy output and determine a first energy controller input.

8. The laser assembly of claim 7, wherein the trigger assembly is electrically coupled to a pulse-width controller configured to receive a first full width half max pulse width and determine a first pulse-width controller input.

9. The laser assembly of claim 1, wherein the sensor includes a photodiode.

10. The laser assembly of claim 1, wherein the trigger assembly is a Q-switch trigger assembly.

11. A laser assembly comprising:
    a laser resonator that emits a first light having a first pulse width;

a trigger assembly electrically coupled to the laser resonator to actuate the laser resonator;

a photodiode configured to detect the first light as the light emits from the laser resonator;

an energy controller electrically coupled to the photodiode and configured to determine a first energy controller input based on an energy output of the first light;

a pulse-width controller electrically coupled to the photodiode and configured to determine a first pulse-width controller input based on a first full width half max pulse width of the first light; and one or more processors coupled to the trigger assembly and photodiode, and configured to:
    actuate the laser resonator to emit a second light having a second pulse width based on the first energy controller input and first pulse-width controller input.

12. The laser assembly of claim 11; wherein the pulse-width controller is configured to determine a time delay between when the trigger assembly communicates an actuation signal to the laser resonator, and when the photodiode detects the first light; and determine the first pulse-width controller input based on the time delay and the first full width half max pulse width.

13. The laser assembly of claim 12, wherein the first pulse-width controller input is based on a proportion between the time delay and the first full width half max pulse width.

\* \* \* \* \*